(12) United States Patent
Trovato et al.

(10) Patent No.: US 9,946,979 B2
(45) Date of Patent: Apr. 17, 2018

(54) METHOD AND SYSTEM FOR FAST PRECISE PATH PLANNING

(75) Inventors: Karen Irene Trovato, Putnam Valley, NY (US); Aleksandra Popovic, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 83 days.

(21) Appl. No.: 12/996,818

(22) PCT Filed: Jun. 19, 2009

(86) PCT No.: PCT/IB2009/052650
§ 371 (c)(1),
(2), (4) Date: Dec. 8, 2010

(87) PCT Pub. No.: WO2009/156931
PCT Pub. Date: Dec. 30, 2009

(65) Prior Publication Data
US 2011/0093191 A1 Apr. 21, 2011

Related U.S. Application Data

(60) Provisional application No. 61/099,223, filed on Sep. 23, 2008, provisional application No. 61/075,886, filed on Jun. 26, 2008.

(51) Int. Cl.
*G01C 21/34* (2006.01)
*G06Q 10/04* (2012.01)
*A61B 17/34* (2006.01)

(52) U.S. Cl.
CPC ........ *G06Q 10/047* (2013.01); *A61B 17/3421* (2013.01); *A61B 2017/3443* (2013.01)

(58) Field of Classification Search
CPC .............. G06Q 10/047; A61B 17/3421; A61B 2017/3443
(Continued)

(56) References Cited

U.S. PATENT DOCUMENTS 5,625,559 A * 4/1997 Egawa ............ G05B 19/41895
701/117
6,560,512 B1 * 5/2003 Rosen .................... B25J 9/1664
700/245
(Continued)

FOREIGN PATENT DOCUMENTS

EP 1867952 12/2007
WO WO2007042986 4/2007

OTHER PUBLICATIONS

Alex Yahja et al., "An Efficient On-Line Path Planner for Outdoor Mobile Robots", Robotics and Autonomous Systems 32 (2000), 2000 Elsevier Science B.V., pp. 129-143.
(Continued)

*Primary Examiner* — Shardul D Patel

(57) ABSTRACT

A system (200) executes a method (130-180) to produce an optimal path for any type of path planning application. In operation, the system (200) constructs a configuration space node structure representing a discretized configuration space including a plurality of states characterized by one or more parameters, and augments the configuration space node structure with discrete parameter values explicitly quantifying each node of the configuration space node structure and/or with heuristic values serving as a search guide through a free space region of the discretized configuration space.

15 Claims, 11 Drawing Sheets

(58) Field of Classification Search
USPC .............................. 701/202, 117, 533, 423
See application file for complete search history.

(56) References Cited

U.S. PATENT DOCUMENTS

| | | | | |
|---|---|---|---|---|
| 6,604,005 | B1* | 8/2003 | Dorst | B25J 9/1666 |
| | | | | 700/254 |
| 6,834,229 | B2* | 12/2004 | Rafiah | G06Q 10/047 |
| | | | | 701/533 |
| 8,014,941 | B2* | 9/2011 | Nagel | G01C 21/34 |
| | | | | 701/423 |
| 8,417,491 | B2* | 4/2013 | Trovato | A61B 90/10 |
| | | | | 703/6 |
| 2008/0075886 | A1* | 3/2008 | Nagase | G21F 9/005 |
| | | | | 427/560 |
| 2008/0099223 | A1* | 5/2008 | Stirm | B25D 11/062 |
| | | | | 173/201 |
| 2008/0234700 | A1* | 9/2008 | Trovato | A61B 90/10 |
| | | | | 606/139 |
| 2008/0270158 | A1* | 10/2008 | Abhyanker | G06Q 30/02 |
| | | | | 705/319 |
| 2011/0093191 | A1* | 4/2011 | Trovato | G06Q 10/047 |
| | | | | 701/533 |
| 2014/0230030 | A1* | 8/2014 | Abhyanker | H04L 63/107 |
| | | | | 726/6 |

OTHER PUBLICATIONS

Trovato, K., "A Planning in Discrete Configuration Spaces of Autonomous System", Thesis. 1996.

* cited by examiner

METHOD AND SYSTEM FOR FAST PRECISE PATH PLANNING

The present invention relates to a method and a system for planning an optimal path with obstacle avoidance. Examples of such path planning applications include, but are not limited to, (1) a planning of a surgical path for an instrument within a patient, (2) a planning of a movement/travel path for a robot, a vehicle, a plane, a ship, etc. within a particular environment, (3) a planning of a flow path through various conditional and unconditional states of an economic system, an emergency system, etc., and (4) a planning of a route path of streets, highways, waterways, etc. over or through a specified body of land and/or water.

Such path planning applications can be performed using the framework taught by Karen I. Trovato, *A\* Planning in Discrete Configuration Spaces of Autonomous System*, University of Amsterdam, 1996.

Specifically, a path planning application must be able to be described in terms of discrete parameters. That is, the path planning application is characterized by key parameters with each parameter having one or more ranges of valid discrete parameter values. A combination of all the possible parameter ranges is called the configuration space, and each state of the configuration space provides a unique setting for each of these parameters.

The allowed actions that cause changes or transitions from one state in the configuration space to another state within a certain range are encapsulated as the 'neighborhood'. In other words, the neighborhood is a collection of permissible successors that represent the core state transitions within a portion or the entirety of the configuration space. Since the configuration space is a discretized space, each state of the configuration space can be considered as 'nodes' in a two-dimensional or three-dimensional graph, and any events or movements in the configuration space that can cause a change between two or more states can be viewed as 'transitions' between the nodes.

The 'neighborhood' also may be determined based upon 'rules of the game', so there may be a few neighbors that are selected by a particular attribute of the task space itself or a physical object/state flow within the task space. Transitions may be based on the environment as well, such as, for example, a one-way street. Assigned to each transition is the cost imposed for changing between an original state and a neighbor state. Therefore the combination of the states in configuration space with the neighborhood transitions between them can be thought of as a graph with the states as nodes and permissible transitions as directed edges.

For many path planning applications, constraints exist that define illegal states, often because of mechanical limitations, interaction with obstacles, or imposed rules. Thus, there may be identifiable forbidden region(s) of nodes in the configuration space. In some graphs, the transitions into these nodes are removed along with the nodes themselves. Alternatively, the nodes may be marked as illegal, or transitions into the node may have infinite (unattainable and high) cost, denoted by $\infty$. Each of these techniques causes a search to avoid the constrained nodes.

With the path planning, a 'goal' position may be mapped to one or more equivalent 'goal' nodes in the discretized configuration space. Multiple 'goal' nodes may exist because the formulation of parameters expressing the system may have more than one solution describing the system 'goal'. For example both left handed and right handed configurations of your arm can reach the same location. The system 'start' is simply transformed to a specific starting node.

Finding the most desirable series of events leading from a current system node to a desired 'goal' is analogous to finding an optimal path of transitions from the current node to the 'goal' node that incurs a minimum cost while avoiding all illegal nodes. The objective of the path planning often has a criterion for success sometimes called a space variant metric, a cost metric, or an objection function (e.g., a fastest, shortest, least expensive, etc.). In many cases, this can be directly translated to a cost incurred for a particular transition between nodes. The desirable series of events therefore can be found by planning a path using the configuration space nodes, transitions, costs, forbidden regions, and 'goal', and by defining or setting a 'starting node'. A graph search method such as A* provides an efficient mechanism to determine the optimal path.

The present invention expands the utilization of the subject framework taught by Trovato in planning an optimal path with obstacle avoidance by facilitating the use of discrete parameter values explicitly quantifying each node of a configuration space node structure.

One form of the present invention is a method for planning an optimal path according to a path planning application. The method involves a construction of a configuration space node structure within a data storage medium, the configuration space node structure representing a discretized configuration space including a plurality of states characterized by one or more parameters. The method further involves an augmentation of the configuration space node structure as constructed within the data storage medium with discrete parameter values explicitly quantifying each node of the configuration space node structure.

A second form of the present invention is a system employing a data storage medium (i.e., any medium for storing data) and a data processing device (i.e., any device for performing operations involving the stored data to yield information) for planning an optimal path according to a path planning application. In operation, the data processing device constructs a configuration space node structure within the data storage medium, the configuration space node structure representing a discretized configuration space including a plurality of states characterized by at least one parameter. The data processing device further augments a construction of the configuration space node structure within the data storage medium with discrete parameter values explicitly quantifying each node of the configuration space node structure.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

The present invention is premised on three (3) primary inventive principles.

First, a discretized configuration space for path planning applications can be made more precise by making each node within the configuration space node structure contain discrete parameter values explicitly quantifying each node of the configuration space node structure rather than relying on discrete parameter values inferred from the indices of the discretized configuration space as is well known in the art. This implies that high resolution computations of the paths can be computed precisely, even in a coarsely discretized configuration space. This further implies that a lower resolution configuration space can be used to save memory, or make previously impossible path planning applications tractable in time and memory.

Second, when necessary, configuration space storage can be separated between obstacle representation and computed states and directions, and allocated 'on demand', so that only expanded nodes contain the full details of the state, such as, for example, floating point accuracy of the traversed state in all N dimensions. Since expansions typically cover far less than an entire configuration space, this savings can be about 20× the nominal configuration space. As such, many path planning applications requiring a 64-bit machine can now use a 32-bit machine.

Third, in the A* algorithm, heuristic values can be used to guide a search through a free space (non-obstacle) area of a discretized configuration space. For path planning application, the fastest non-holonomic A* algorithm execution can be achieved if the heuristic values first estimate the exact distance from the goal through free space that factors in the distance around obstacles.

It is to be understood by persons of ordinary skill in the art that the following description of FIGS. 1-18 are provided for purposes of illustration of the aforementioned inventive principles of the present invention in general terms with specific yet straightforward examples and not for limiting the practice of such inventive principles. In particular, unnecessary detail of known functions and operations may be omitted from the description of the inventive principles herein so as not to obscure the present invention. Nonetheless, an artisan will understand how to practice the inventive principles of the present invention to any type of path planning application (i.e., surgical tool path planning, vehicle path planning, economic system path planning, etc.) and will further understand that there are many variations that lie within the spirit of the present invention and the scope of the appended claims.

Figure 1:
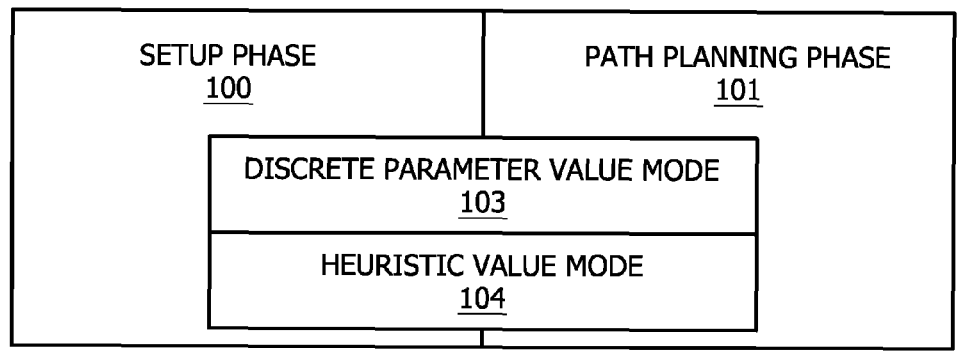
FIG. 1 illustrates a block diagram of a discrete parameter value mode and a heuristic value mode in accordance with present invention.

FIG. 1 illustrates a setup phase 100 and a path planning phase 101 for any type of path planning application including, but are not limited to, (1) a planning of a surgical path for an instrument within a patient, (2) a planning of a movement/travel path for a robot, a vehicle, a plane, a ship, etc. within a particular environment, (3) a planning of a flow path through various conditional and unconditional states of an economic system, an emergency system, etc., and (4) a planning of a route path of streets, highways, waterways, etc. over or through a specified body of land and/or water.

In general terms, setup phase 100 may minimally involve (1) a construction of a configuration space node structure representing a discretized configuration space including a plurality of states characterized by one or more parameters, (2) an identification of a neighborhood encapsulating all of the allowed actions that cause changes or transitions between states in the discretized configuration space, and (3) a formulation of a metric representing the criterion for success in planning a path through the discretized configuration space. Furthermore, in general terms, path planning phase 101 may minimally involve (1) an identification or definition of a seed node within the discretized configuration space, and (2) a utilization of the seed node to initiate a propagation of cost waves through the configuration space node structure based on the metric to find the most desirable series of events between a start node and a goal node.

The present invention introduces a discrete parameter value mode 103 that can be incorporated in setup phase 100 and/or path planning phase 101 of the path planning application. In general terms, a configuration space node structure includes a plurality of nodes with each node being at a different discrete location, flow point, etc. in the discretized configuration space as characterized by the parameter(s), and discrete parameter value mode 103 provides for the use of discrete parameter values explicitly quantifying the nodes of the configuration space node structure as opposed to the inferred discretized values from the indices of the discretized configuration space as is well known in the art. For purposes of the present invention, the term "explicitly quantifying" is broadly defined herein as a precise expression of a number, a measure, a quantity or any other applicable parameter as related to the nodes in a particular configuration space node structure.

Figure 2:
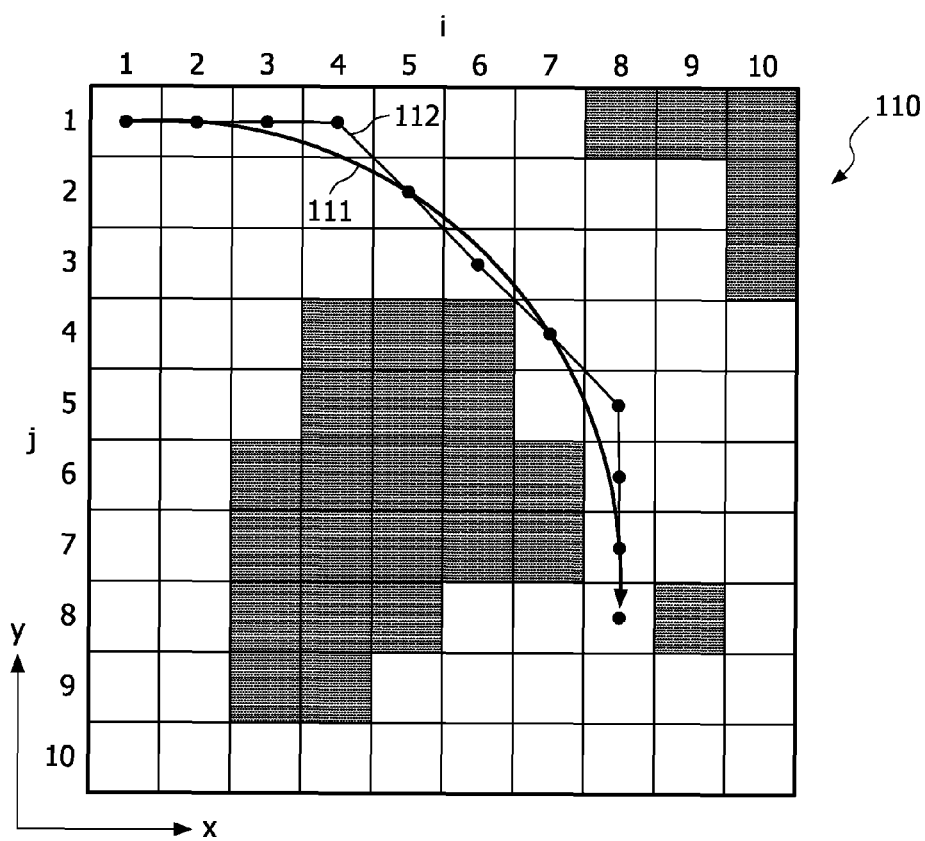
FIG. 2 illustrates an exemplary discretized configuration space displaying the discrete parameter value mode of the present invention.

For example, FIG. 2 illustrates a path 111 within a discretized configuration space 110 having a 10×10 two-dimensional arrangement of states characterized by x and y location parameters. As known in the art, a reliance on the discrete parameter values being inferred from the i,j indices yields a 1 unit cost from an unobstructed transition between direct neighbors and a 1.4 unit cost from an unobstructed transition between diagonal neighbors. However, instead of relying on the discrete parameter values inferred from the i,j indices of discretized configuration space 110 as exemplarily shown by line 112, discrete parameter value mode 103 uses discrete parameter values explicitly quantifying the x and y location parameters of path 111 for the configuration space node structure as will be further explained herein. This results is a precise cost calculation from any type of node transition within the configuration space node structure.

Figure 3:
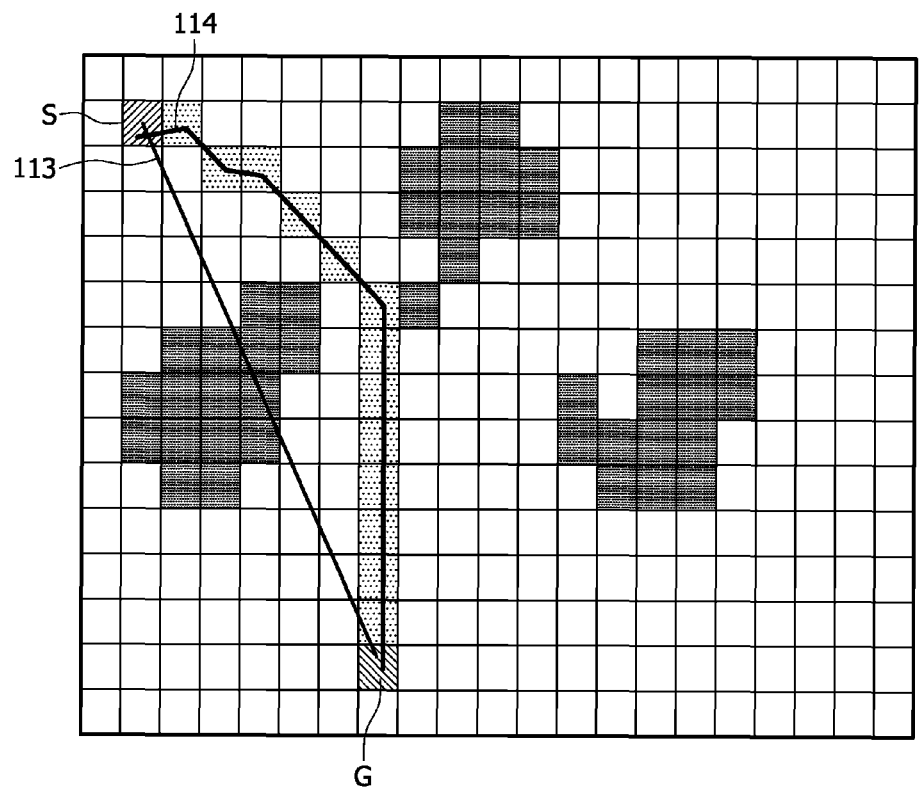
FIG. 3 illustrates an exemplary discretized configuration space displaying the heuristic value mode of the present invention.

The present invention further introduces a heuristic value mode 104 that can be incorporated in setup phase 100 and/or path planning phase 101 of the path planning application. In general terms, heuristic value mode 104 provides for the use of heuristic values representing a search guide through a free space region of a discretized configuration space. In particular, the heuristic values estimate the exact distance from a goal or goals through the free space region that factors in the distance around obstacles to thereby obtain preferred admissible heuristic values for the configuration space node structure. For example, FIG. 3 illustrates an exemplary admissible heuristic 113 based on a straight-line Euclidean distance between a seed node S and a goal node G that is not preferred when used to guide a non-holonomic path since there is an obstacle on this path. By comparison, an admissible heuristic 114 factors in the distance around the obstacle and is therefore a preferred and admissible heuristic for non-holonomic path planning purposes.

Various exemplary embodiments of discrete parameter value mode 102 and heuristic value mode 103 as shown in FIGS. 4-18 will now be described for the purpose of facilitating a further understanding of the inventive principles of the present invention whereby those having ordinary skill in the art will appreciate the various benefits of the present invention including, but not limited to, an improvement in the inherent discretization error of a configuration space node structure that is achieved by discrete parameter value mode 102 and an improvement in time efficiency while searching for an optimal path that is achieved by heuristic value mode 103.

A. Discrete Parameter Value Mode (Data Acquisition)

Figure 4:
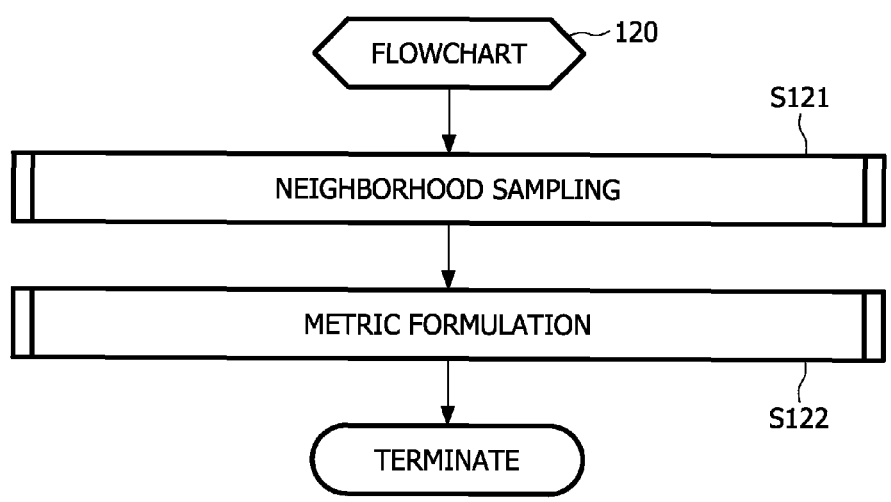
FIG. 4 illustrates a flowchart representative of a discrete parameter value acquisition method in accordance with the present invention.

FIG. 4 illustrates a flowchart 120 representative of a discrete parameter value acquisition method of the present invention. The objective of this method is to acquire a practical set of actual discrete parameter values of the states of a discretized configuration space during setup phase 101 (FIG. 1) of a path planning application to facilitate an optimal search during path planning phase 102 (FIG. 1) of the path planning application.

Figure 5:
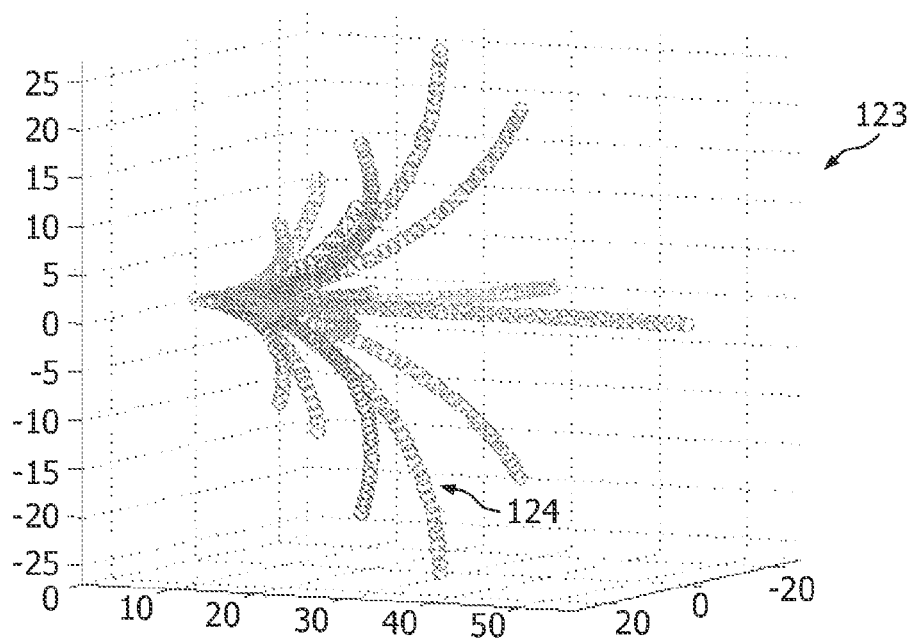
FIG. 5 illustrates an exemplary non-holonomic neighborhood as known in the art.
Figure 6:
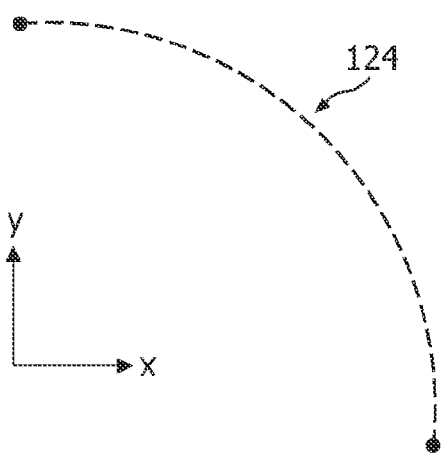
FIG. 6 illustrates an exemplary sampling of a neighborhood thread in accordance with the present invention.

A stage S121 of flowchart 120 encompasses a sampling of a neighborhood encapsulating all of the allowed actions that cause changes or transitions between states in the discretized configuration space. For example, FIG. 5 illustrates an exemplary non-holonomic neighborhood 123 of threads for a bronchoscope or an active or nested cannula. Stage S121 can employ a sampling process for converting the continuous threads of the neighborhood 123 into numeric sequences of discrete parameter values explicitly quantifying the x,y,z location parameters of each node, such, as for example, a Nyquist-Shannon sampling of the threads based on an 'x', 'y' or 'z' smallest unit specification that would provide discrete x,y,z values for each node. FIG. 6 illustrates an exemplarily sampling of a thread 124 based on an x unit specification.

A stage S122 of flowchart 120 encompasses a formulation of a chosen metric as a function of the explicit discrete parameter values acquired during stage S121. For example, using the discretized configuration space shown in FIG. 1, the metric can be a locally Euclidean metric whereby, at each state (i,j), the cost of the transition to a neighbor state removed from state (i,j) by direction arrow $\overline{(di,dj)}$ is given by $\sqrt{dx^2+dy^2}$ where dx and dy are the explicit discrete parameter values in terms of the x,y location for the node corresponding to state (i,j).

Referring to FIGS. 1 and 4, flowchart 120 can be implemented during setup phase 100 and/or path planning phase 101 as appropriate for the specific path planning application.

B. Discrete Parameter Value Mode (Data Management)

Figure 7:
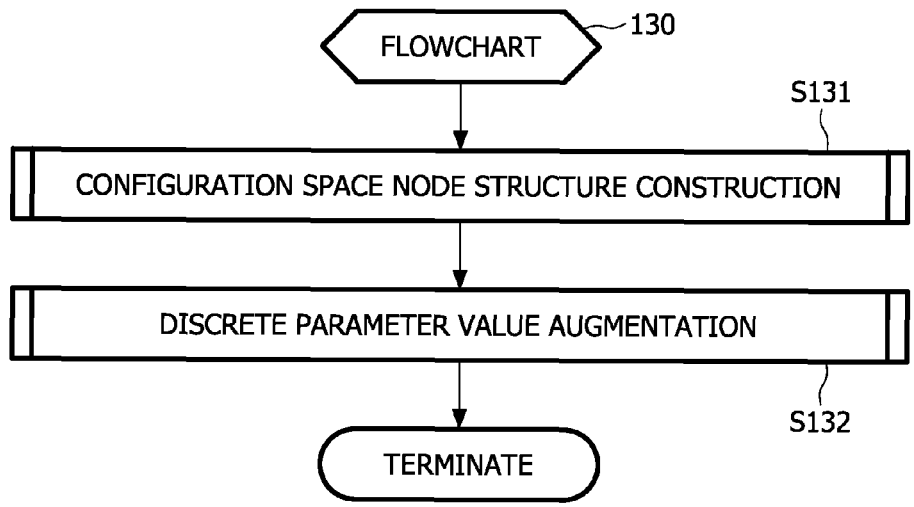
FIG. 7 illustrates a flowchart representative of a discrete parameter value management method in accordance with the present invention.

FIG. 7 illustrates a flowchart 130 representative of discrete parameter value management method of the present invention. The purpose of this method is to augment configuration space node structure with the discrete parameter values without any negative impact on the speed and memory capacities of a system executing the method.

A stage S131 of flowchart 130 encompasses a construction of a configuration space node structure within a data storage medium of any type whereby the constructed configuration space node structure can be augmented with discrete parameter values explicitly quantifying the nodes during a stage S132 of flowchart 130. In practice, the construction scheme for the configuration space node structure selected for stage S131 is dependent upon many factors, in particular the configuration space storage requirements for the precision needed in the given path planning application and the actual and relative number of free space nodes that would require the explicit discrete parameter values to achieve the desired precision. To facilitate an understanding of flowchart 130, three (2) exemplary construction schemes will now be described herein.

1. Baseline Construction

The first construction scheme, known only herein as "the baseline construction", is appropriate for a discretized configuration space having an approximately equal number and even distribution of free space nodes and obstacle nodes, such as, for example, the discretized configuration space 110 shown in FIG. 2. This can be determined from a reading of an obstacle map to determine the number of free space nodes relative to the obstacle nodes, or by the inherent nature of the path planning application.

Figure 8:
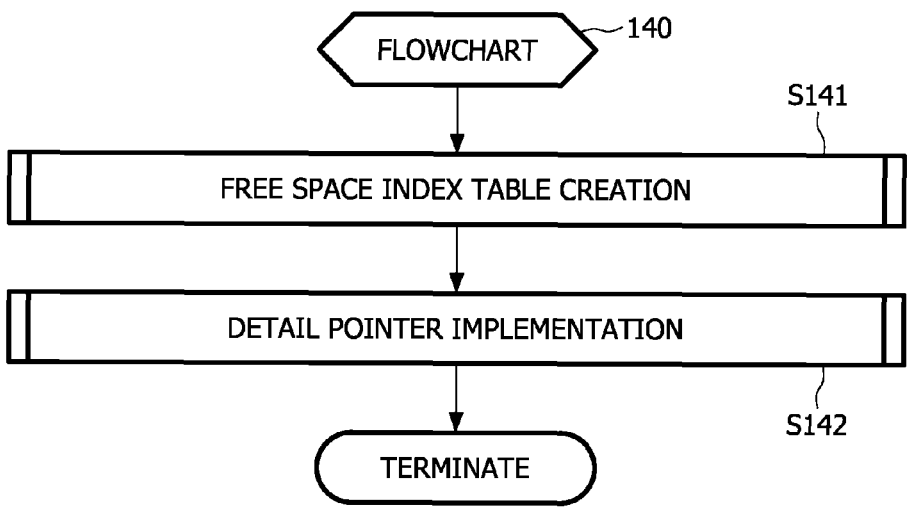
FIG. 8 illustrates a flowchart representative of a baseline construction method in accordance with the present invention.

For example, FIG. 8 illustrates a flowchart 140 representative of a baseline construction method of the present invention. A stage S141 of flowchart 140 encompasses a creation of an indexed table to hold all of the free space nodes, and a stage S142 of flowchart 140 encompasses a construction of a configuration space node structure having a detail pointer for each free space node that points to corresponding discrete parameter values as well as any other relevant detail information for the free space node. The following is an example of a baseline construction of a configuration space node structure with a detail pointer:

```
typedef struct csnode {
    COSTTYPE cost_to_goal;// float
    struct csnode *vector;
    int heap_location;  //index into heap (tree[i])
    CSDETAILNODE *details; // pointer where details reside.
} CSNODE;
typedef struct csdetailnode {
    COSTTYPE h1 ; // heuristic float value. Can be computed on the fly,
    or stored
```

-continued

```
ORIENTATIONTYPE alpha, theta, phi; // rotation about x, y, z
XYZMM Xmm, Ymm, Zmm;//float
THREADTYPE thread; // each thread maps to a radius and
   orientation
CSNODE* myCSNODE; // pointer back to the CSNODE that owns
   these details
} CSDETAILNODE;
```

In this baseline construction example, core configuration space information (CSNODE) includes the cost_to_goal indicative of the remaining cost to reach the nearest goal, the vector pointing to the next node to be reached while heading toward the nearest goal, heap_location that is used during sorting, and the detail pointer pointing to detail configuration space information (CSDETAILNODE). By comparison, the detail configuration space information (CSDETAILNODE) includes a heuristic float value, the node orientation in three (3) dimensions, the explicit discrete parameter values indicative of the actual x,y,z location of the node within the discretized configuration space, and a pointer back to the core configuration space information (CSNODE).

In an example path planning application for the configuration space of the lung, such as for a bronchoscope maneuver or active cannula configuration, a 512×512×600 configuration space node structure as defined above is used. In this example, a program can generate a comparison of the options. It computes the memory required for a 'fully loaded' configuration space having all variables in each location, and the memory required for 'fully loaded' configuration space broken up into the core configuration space information and detailed configuration space information as previously described herein. The following is an exemplary output of the program:

CSnodes: 157,286,400
    Size of Each ORIG is: 80 bytes
    Totaling 12,582,912,000 bytes
    NOW:
    Size of each NEW CS node is 24
    Total CS bytes=3,774,873,600
    Number of Free space elements: 725,038 at bytes each for DETAILS: 64
    Details total bytes=46,402,432
    Totaling 3,821,276,032
    Better to break CS into Details, saving: 8,761,635,968

Consequently, the nominal (original) configuration space can be reduced in size from 12 gigabytes to less than 4 gigabytes. Since the algorithm runs dramatically faster if the entire configuration space node structure can fit into memory without paging, this high-resolution problem can be run on a current 64 bit machine without difficulty. Please note that program itself requires memory and heap space required for sorting.

Referring to FIGS. 7 and 8, stage S132 of flowchart 130 (FIG. 7) can implement a cost wave propagation in the configuration space node structure to fill a portion or an entirety of the configuration space node structure constructed in accordance with flowchart 150 (FIG. 8) with cost values according to a chosen metric. In this case, the cost values are a function of the explicit discrete state parameters whereby the configuration space node structure is augmented with the explicit discrete state parameters as the detailed configuration space information of a seed free space node or an improved free space node is only allocated during the cost wave propagation as will be further explained herein.

Figure 9:
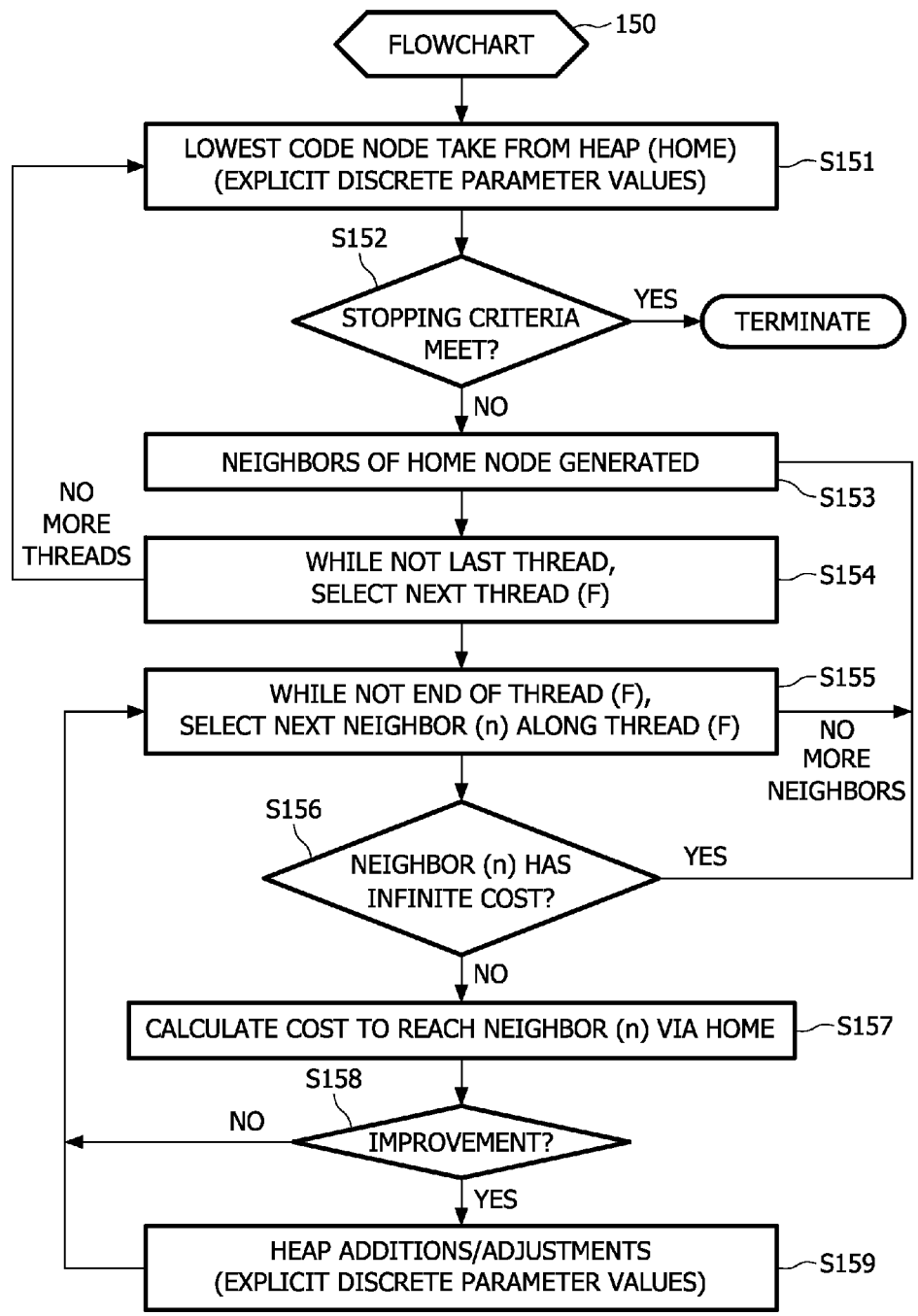
FIG. 9 illustrates a flowchart representative of A* algorithm for determination of an optimal path from a 'seed' node to a 'goal' utilizing explicit discrete state parameters in accordance with the present invention.

For example, FIG. 9 illustrates a flowchart 150 representative of A* algorithm for determination of an optimal path from a 'seed' node to a 'goal' utilizing explicit discrete parameter values in accordance with the present invention based on the neighborhood 123 as shown in FIG. 2. Specifically, a 'seed' node is placed into the heap in order to begin cost wave propagation, or A*. The heap is a balanced binary tree that maintains the lowest cost value at the root. A step S151 of flowchart 150 encompasses the lowest cost node being taken from the heap. The node taken from the heap is called 'home'. It is assumed that well-known algorithms are employed to ensure that the heap remains correct.

Step S151 further encompasses the details pointer of the 'seed' being used to allocate a CSDETAILNODE for the home node to thereby obtain the detailed configuration space information of the home node, particularly the explicit discrete parameter values (XYZMM) of the home node. This provides the precession desired for the cost wave propagation without any negative impact on the speed and memory capacities of a system executing flowchart 150.

A step S152 of flowchart 150 encompasses a testing of a "stopping criterion" is tested. There are many tests that can be performed to determine if the process may stop. The "stopping criterion" may include, but not limited to, a test of whether the heap is empty and (2) a test of whether the current ('home') node's cost_to_goal value is greater than the (target) 'start' or 'goal'. This enables the search to terminate before the entire space is filled, yet nonetheless it does give the optimal path between the 'start' and 'goal'.

If the 'stopping criterion' is met, then flowchart 150 is terminated. Otherwise, if the "stopping criterion" is not met, then a step S153 of flowchart 150 encompasses a generation of the neighborhood of permissible transitions. The neighbors of the 'home' node are calculated based on the 'home' node's orientations given by its alpha, theta and phi as well as its 'home' x, y, z location. The neighborhood results from rotating the nominal neighborhood by alpha, theta and phi, and then translating the already rotated neighborhood relative to the 'home' node's x, y, z location. Methods for rotation and translation of points are well known to those skilled in the art.

In the case where a pixel is not perfectly square during step S154, such as in CT images, where the ratio of x:y:z may be 1:1:1.3 for example, the rotations are performed, and then the values are scaled. The resulting neighborhood is then translated to the location of the current expanding node.

Once the neighbors for the current 'home' node are computed, flowchart 150 proceeds to a step S154 where the next thread (F) of the neighborhood is chosen, if any. If there are no more threads, then flowchart 150 returns to step S151. Otherwise, if there is a thread (F), then flowchart 150 proceeds to a step S155 to chose next neighbor (n) along the thread (F) if any.

If there are no more neighbors along this thread (F), then flowchart 150 returns to step S151. If there is another neighbor (n), then flowchart 150 proceeds to a step 156 to test the cost value of the neighbor. If it is infinite, or there is another indication that the neighbor is not passable, then flowchart 150 returns to step S151. Another indication might be that the neighbor has a cost value higher than some pre-determined threshold, which is less than infinity, but too high to pass. This threshold may be a function of the current distance traveled (at the 'home' node), for example.

If the neighbor does not have infinite cost, the flowchart 150 proceeds to step S157 to calculate the proposed new cost F(n') for the new neighbor. Since the neighbor may already have a cost, it is denoted F(n'). In the A* algorithm, a heuristic h(n) may be used to guide the search. A perfectly valid value is h=0, however, which causes the space to fill from all 'seed' nodes until the 'stopping criterion' is satisfied/true. Preferably, heuristic values are in accordance with FIG. 14 as will be subsequently described herein.

Flowchart 150 thereafter proceeds to a step S158 to compare the calculated cost F(n') with the pre-existing cost at n, F(n). If calculated F(n') is greater than pre-existing cost F(n), then it is more costly to reach n via the 'home' node than whatever was determined previously (i.e., there is no improvement), and flowchart 150 returns to step S153. If the calculated cost F(n') is less than pre-existing cost F(n), then this value is an improvement over prior directions whereby flowchart 150 proceeds to step S159 to add the neighbor node to the heap, or if the neighbor node is already on the heap, then the value of such node is updated and the heap adjusted. In the case where the improving neighbor node is added to the head, a CSDETAILNODE is allocated for the neighbor node to thereby obtain the detailed configuration space information of the neighbor node, particularly the explicit discrete parameter values (XYZMM) of the neighbor node. Again, this provides the precession desired for the cost wave propagation without any negative impact on the speed and memory capacities of a system executing flowchart 150.

Step S159 further encompasses the new cost_to_goal being assigned to n, as is a new alpha, theta and phi. The values of alpha, theta and phi are calculated by rotating the nominal node's theta and phi to the parent node's theta and phi with the value of alpha being computed from the current thread. The revised vector leading the best way to the 'seed' node, is assigned a pointer to 'home'. Optionally, but preferably, the number of the thread is stored. This minimizes computation later on during path following, since the number of the thread maps directly to the control parameters, that is, for example, the amount that a bronchoscope is turned up/down and left/right, or the shape and relative orientation of a nested cannula, or the steering and forward/reverse of a car.

Upon the stopping criteria being met, the resulting planned path will be more precise and obtained faster than previously achieved in the art.

2. Sparse Free Space Construction

Figure 10:
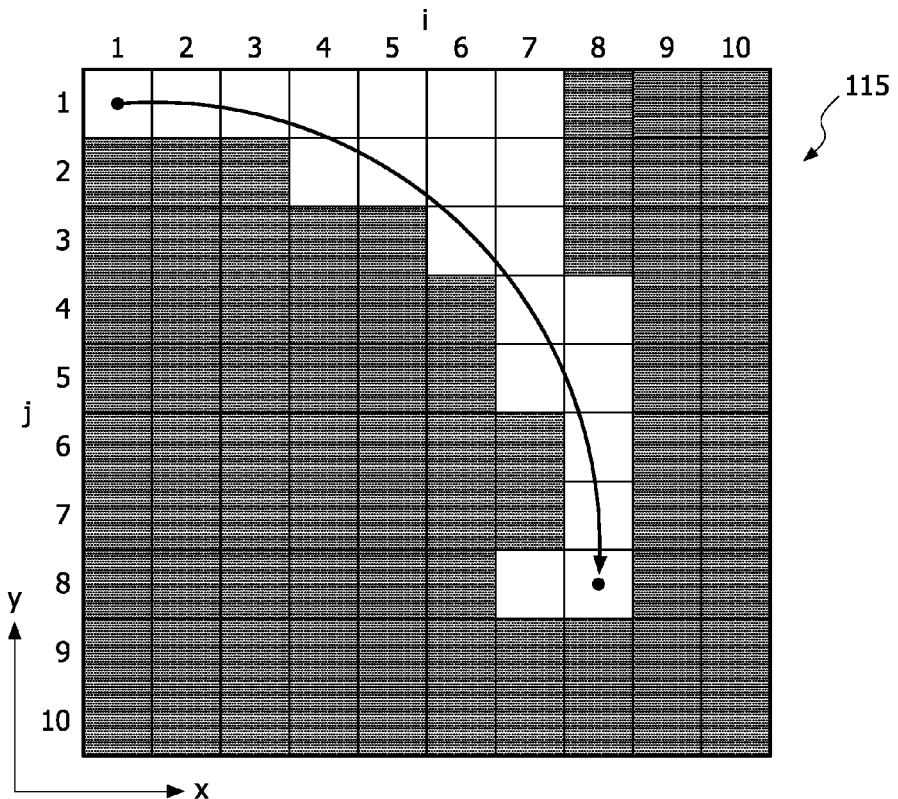
FIG. 10 illustrates an exemplary discretized configuration space having a sparse representation of free space nodes.

The second construction scheme, known only herein as "the sparse free space construction", is appropriate for a configuration space having a significant degree of more obstacle nodes than free space nodes, such as, for example, a discretized configuration space 115 shown in FIG. 10. This can be determined from a reading of an obstacle map to determine the number of free space nodes relative to the obstacle nodes, or by the inherent nature of the path planning application, such as, for example, a car parking planning or a lung navigation planning. For a sparse free space construction that complies with the configuration space requirements for the precision needed in the given path planning application, an entire data set can actually be stored into the details section for each free space node while obstacle nodes can point to the same NULL location.

Figure 11:
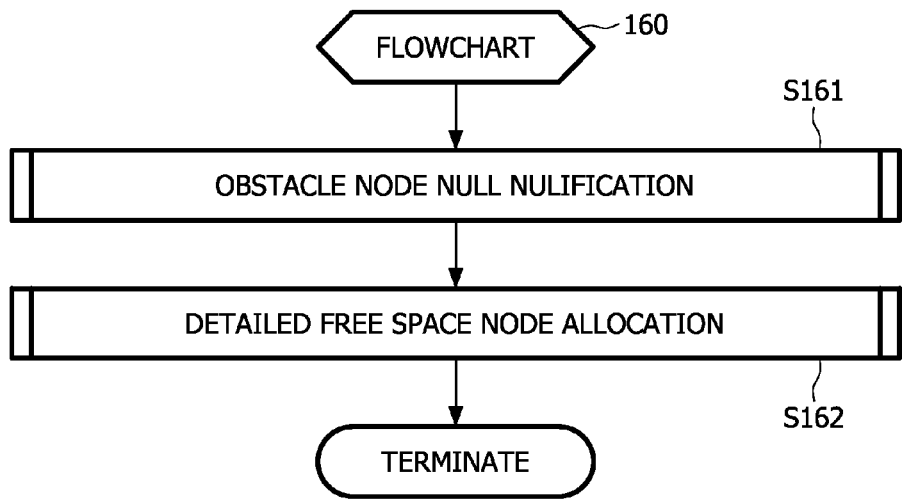
FIG. 11 illustrates a flowchart representative of a sparse free space construction method in accordance with the present invention.

For example, FIG. 11 illustrates a flowchart 160 representative of a sparse free space construction method of the present invention. A stage S161 of flowchart 160 encompasses a creation of a NULL location with each obstacle node pointing to the NULL location or alternatively a default obstacle node indicating NULL can be created, and a stage S162 of flowchart 160 encompasses each free space node including all detail configuration space information, particularly the explicit discrete parameter values. The following is an example of a sparse free space construction of pre-allocated detailed free space nodes for a configuration space node structure:

```
typedef struct csnode {
    COSTTYPE cost_to_goal;// float
    struct csnode *vector;
    int heap_location; //index into heap (tree[i])
    ORIENTATIONTYPE alpha, theta, phi; // rotation about x, y, z
    XYZMM Xmm, Ymm, Zmm;//float
    THREADTYPE thread; // each thread maps to a radius and
        orientation
    COSTTYPE h1 ; // heuristic float value. Can be computed on the fly,
        or stored
} CSNODE;
```

This sparse free space construction makes use of the sparse nature of a three-dimensional configuration space and the fact that any forbidden (obstacle) state does not need to store directions, cost_to_goal or any information other than the fact that it is impassable. Similarly, the entire data set can actually be stored into the details section, leaving only the detailIndex in the configuration space.

At first this may appear to only increase the memory required, since the index is overage and entire set of data is stored in details. However, nodes that are obstacles can point to the same location (such as NULL), in order to save the overhead of details. If there are many obstacles, this can save a great deal of space. Using this technique may require about half a gigabyte of memory.

There are 512×512×600=157,286,400 configuration states, for example, each having only an index. For fewer than 4.2 million free space states, a 4 byte integer or pointer can provide the index requiring a total of 629,145,600 bytes. If there are fewer than 65536 states, a 2 byte integer will clearly suffice. For this application, there are 725,038 free space nodes, each requiring 80 bytes. All together, this memory requirement is 687,148,640 bytes, making the application quite tractable in a 32-bit machine.

This savings in memory however, will increase the access time for the variables moved to details. The first priority is to ensure that the configuration space fits within local (high-speed) memory (RAM), since paging in this application may cause it to be extraordinarily slow.

Referring to FIGS. 7 and 11, stage S132 of flowchart 130 (FIG. 7) can implement a cost wave propagation in the configuration space node structure to fill a portion or an entirety of the configuration space node structure constructed in accordance with flowchart 160 (FIG. 11) with cost values according to a chosen metric. In this case, the cost values are a function of the explicit discrete state parameters whereby the configuration space node structure is augmented with the explicit discrete state parameters prior to the cost wave propagation. For example, all of the detailed free space nodes would be pre-allocated prior to an execution of the A* algorithm for determination of an optimal path from a 'seed' node to a 'goal' in accordance with flowchart 150 shown in FIG. 9.

3. Sparse Obstacle Construction

Figure 12:
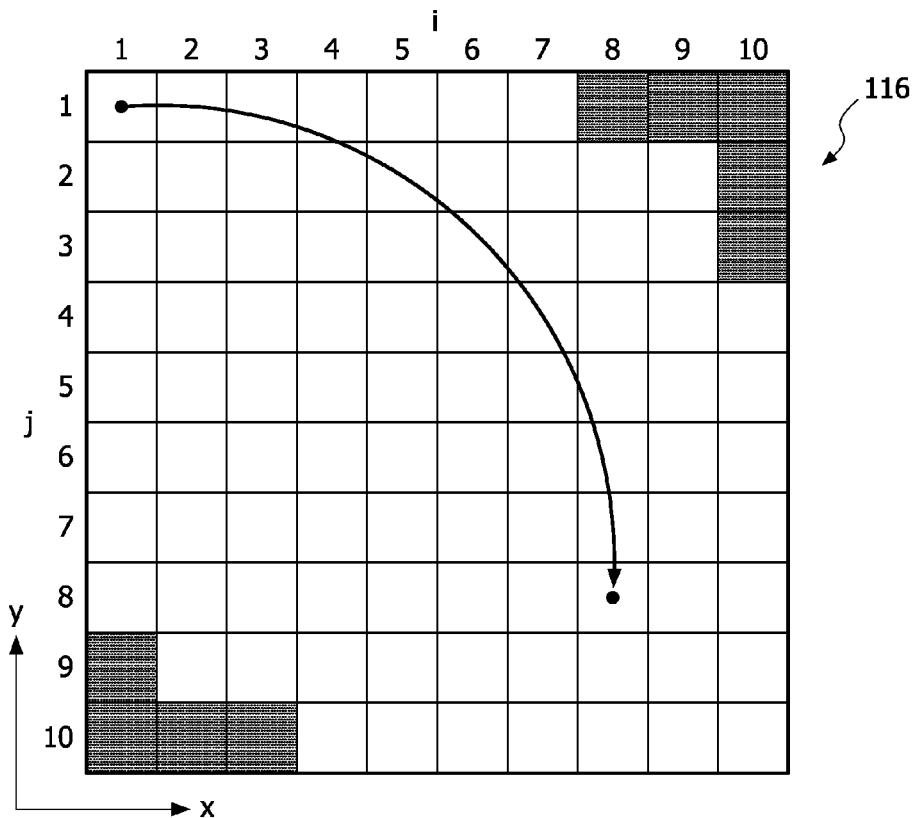
FIG. 12 illustrates an exemplary discretized configuration space having a sparse representation of obstacle nodes.

The third construction scheme, known only herein as "the sparse obstacle construction", is appropriate for a configuration space having a significant degree of more free space nodes than obstacle nodes, such as, for example, a discretized configuration space 116 shown in FIG. 12. This can be determined from a reading of an obstacle map to determine the number of free space nodes relative to the obstacle nodes, or by the inherent nature of the path planning application, such as, for example, an open gymnasium, airspace or laparoscopic surgery. For a sparse obstacle construction that complies with the configuration space requirements for the precision needed in the given path planning application, an entire data set can actually be stored into an on-demand allocated details section for each free space node while obstacle nodes can point to the same NULL location.

Figure 13:
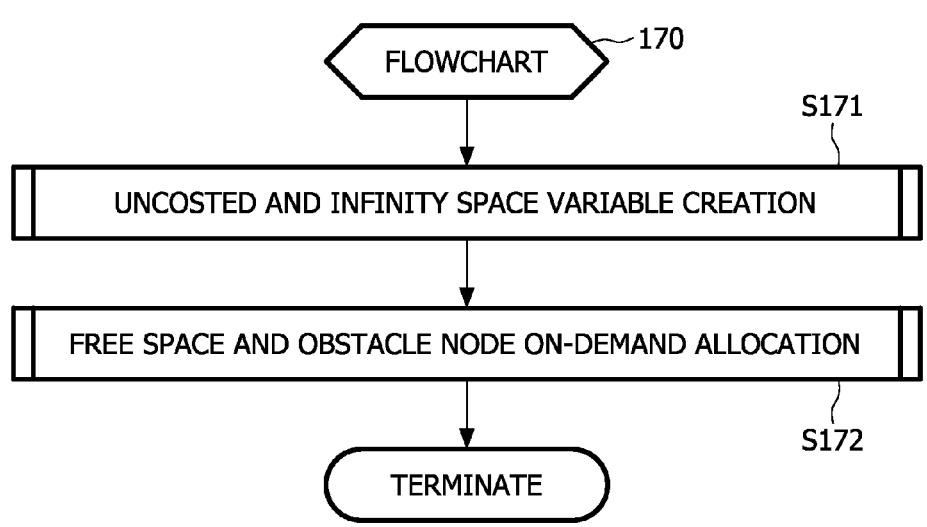
FIG. 13 illustrates a flowchart representative of a sparse obstacle construction method in accordance with the present invention.

For example, FIG. 13 illustrates a flowchart 170 representative of a sparse obstacle construction method of the present invention. A stage S171 of flowchart 170 encompasses a creation of an Uncosted space variable for free space nodes and an Infinity space variable for obstacle nodes, and a stage S172 of flowchart 170 encompasses each free space node including all configuration space information, particularly the explicit discrete parameter values, being allocated on demand. The following is an example of a sparse obstacle construction of detailed free space nodes for a configuration space node structure:

```
typedef struct csnode {
    CSDETAILNODE *details; // pointer where details reside.
} CSNODE;
typedef struct csdetailnode {
    COSTTYPE cost_to_goal;// float
    struct csnode *vector;
    int heap_location;  //index into heap (tree[i])
    COSTTYPE h1 ; // heuristic float value. Can be computed on the fly,
    or stored
    ORIENTATIONTYPE alpha, theta, phi; // rotation about x, y, z
    XYZMM Xmm, Ymm, Zmm;//float
    THREADTYPE thread; // each thread maps to a radius and
    orientation
    CSNODE* myCSNODE; // pointer back to the CSNODE that owns
    these details
} CSDETAILNODE;
```

In the context of a sparse obstacle representation, if the space is a three-dimensional neighborhood, which contains two (2) adjacent neighbors for each dimension, plus the diagonals, the overall 'diameter' of the neighborhood might be estimated as three (3). With a Euclidean metric and no obstacles, the expanded path would be the volume of nodes in a pi*D*length in a continuous space; but it is not, it is discretized. More properly, there are eight (8) neighbors over the length. If the configuration space is the one above, with 512×512×600=157,286,400 configuration states, then a 4 byte integer requires a total of 629,145,600 bytes for the base configuration space. For a path from one corner to the opposite diagonal, the center of the path is about 940=sqrt $(512^2+512^2+600^2)$, assuming with a length ratio of 1:1:1 (cubic voxels). The worst case possible is a chosen path is mostly diagonals. If there are eight (8) neighbors at each increment, then the total memory requirement might only be for about 7520 'detailed' states. This means that the entire problem may be solved in as little as 602K plus the basic configuration space of 629 megabytes. Compared to the earlier use of configuration spaces, the same space would require 12.5 Gigabytes.

Referring to FIGS. 7 and 13, stage S132 of flowchart 130 (FIG. 7) can implement a cost wave propagation in the configuration space node structure to fill a portion or an entirety of the configuration space node structure constructed in accordance with flowchart 170 (FIG. 13) with cost values according to a chosen metric. In this case, the cost values are a function of the explicit discrete state parameters whereby the configuration space node structure is augmented with the explicit discrete state parameters as the entire data set of a seed free space node or an improved free space node is allocated 'on-demand' during the cost wave propagation, such as, for example, in accordance with respective stages of S151 and S159 of flowchart 50 as shown in FIG. 9 and previously described herein.

C. Heuristic Value Mode

Referring again to FIG. 1, a realistic admissible heuristic is provided by heuristic value mode 103 for guidance of the A* search in the space with obstacles. The heuristic significantly improves time efficiency of the algorithm. In particular, heuristic value mode 103 pre-compute and store heuristic values for every node of the free-space during setup phase 100 and use those values during path planning phase 101, particularly for non-holonomic 6D planning. As will be shown, heuristic value mode 103 saves time and allows multiple paths to be planned efficiently.

Figure 14:
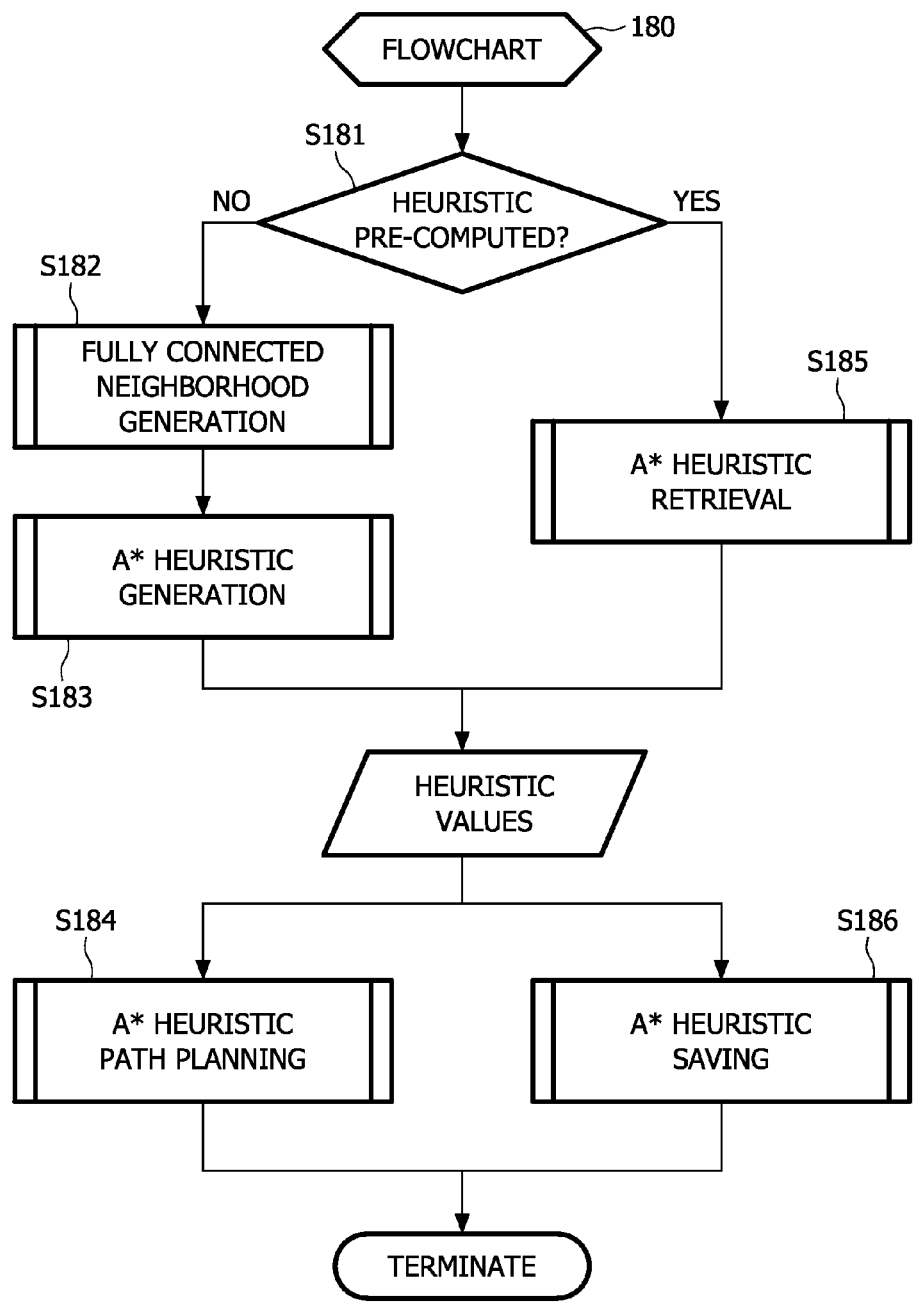
FIG. 14 illustrates a flowchart of a heuristic value generation and retrieval method in accordance with the present invention.

FIG. 14 illustrates a flowchart 180 representative of a heuristic value generation and retrieval method in accordance with the present invention. Generally, the heuristic represents distance from the goal through free space computing in the distance around obstacles as opposed to the direct Euclidean distance as shown in FIG. 3. Additionally, the heuristic can be pre-computed from a configuration space of free space and obstacles only once or recomputed as needed whereby the heuristic can be used repeatedly thereafter for the same configuration space for planning different paths.

Figure 15:
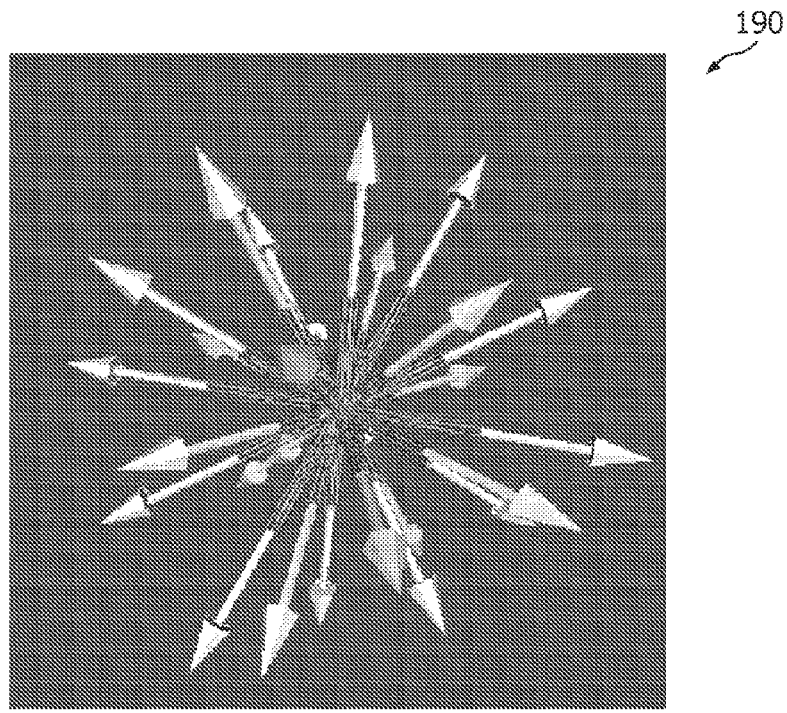
FIG. 15 illustrates an exemplary fully connected neighborhood in accordance with the present invention.

Specifically, a stage S182 of flowchart 180 encompasses a configuration of a fully connected neighborhood that allows the algorithm to visit all free space points in the configuration space, thus—to calculate the heuristic in every state of the free space. A node in the center of the neighborhood is the best node for facilitating a fully connected neighbor in the free space region. FIG. 15 illustrates an example of a fully connected neighborhood 190 for heuristic calculation consisting of twenty-six (26) nodes connected to a node at the center of the neighborhood.

A stage S183 of flowchart encompasses a generation of the heuristic based on the fully connected neighborhood of stage S182 (e.g., FIG. 15). For example, an implementation of flowchart 150 (FIG. 9) as previously described herein can be modified two ways to ensure a proper heuristic is generated based on the fully connected neighborhood. The first modification is a change in algorithm initialization whereby a seed or seeds must be defined for the start of the A* algorithm. This may be a single state, or a set of states, for example the entire plane at the trachea. A second modification is a change in stopping criteria whereby the algorithm is stopped if all nodes in free space are visited, such as, for example, all free space nodes along a plane of the trachea is reached.

Figure 16:
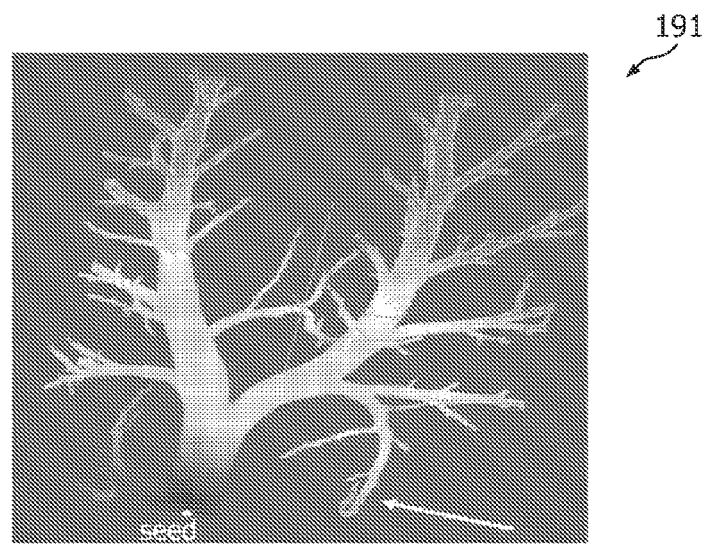
FIG. 16 illustrates an exemplary computed heuristic for all free space points in a bronchial tree in accordance with the present invention.

A stage 186 of flowchart 180 saves the result of stage S183 during setup, which is a configuration space with a computed heuristic value in every state of the free space, such as, for example, an exemplary computed heuristic for all free points in a bronchial tree 191 as shown in FIG. 16. This information can be saved in a three-dimensional image in memory or on a hard drive (HD). For example the data may be in raw format or in Analyze image format. These are preferred because floating point can be stored in these formats, rather than only 12 bit integers common for DICOM, for example. Information in every image element (configuration state), i.e. in every location of the free space, can be retrieved at a stage S185 during path planning. Pre-computation of heuristics allows multiple path planning (different goal points from the same seed) with single heuristic computation.

Figure 17:
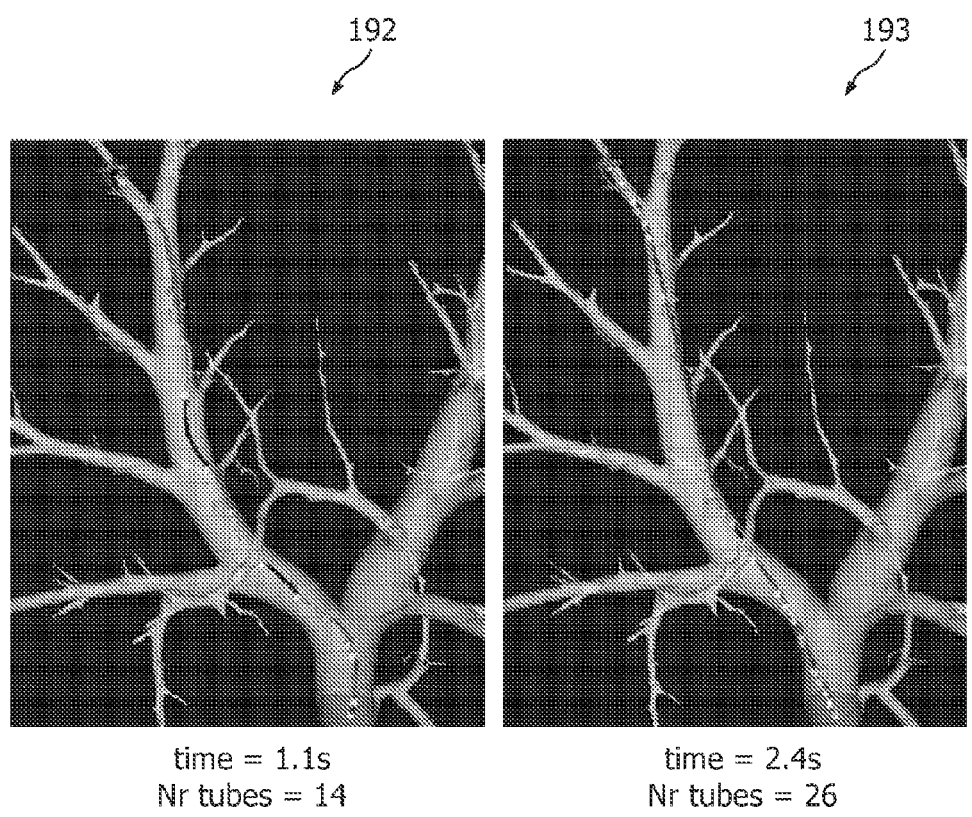
FIG. 17 illustrates an exemplary path planned with a heuristic in accordance with the present invention and with a simple Euclidean heuristic as known in the art.

A stage S184 of flowchart 180 encompasses the use of the heuristic to guide the search in the configuration space. In case when the heuristic is zero (h(n)=0), no guidance is provided and the algorithm visits all points in the free space. With a heuristic that avoids obstacles, a better approximation than a pure Euclidean measure can be used to guide a non-holonomic neighborhood. In nested cannula configuration, this also influences the number of tubes needed to reach the goal. For example, FIG. 17 shows an example 192 of path planning in a nested cannula configuration with a heuristic generated in accordance with flowchart 180, and an example 193 of a path planning in a nested cannula configuration with a heuristic generated in a pure Euclidean measure as known in the art. Using the heuristic of the present invention as shown on the left, computation time is reduced by more than 50% and number of tubes is reduced by more than 40% as compared to the Euclidean heuristic 193. Further, the heuristic has proved to be able to be computed in less than 0.5 seconds, a net savings of time.

D. Plan Planning System

Figure 18:
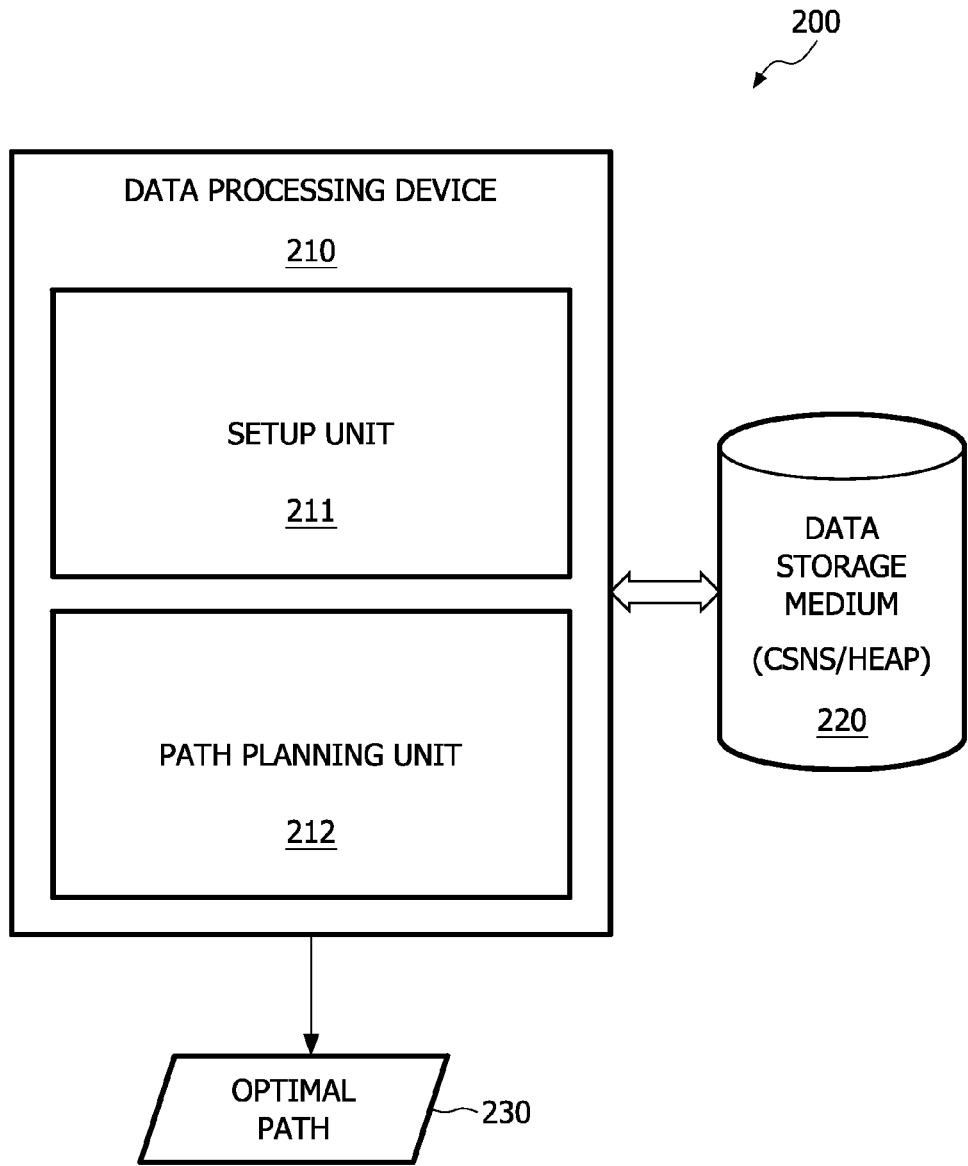
FIG. 18 illustrates a block diagram of a system in accordance with the present invention.

Referring now to FIG. 18, a system 200 is illustrated for a path planning application in accordance with the present invention. The system 200 includes a data processing device 210 and a data storage medium 220. Data processing device 210 employs a setup unit 211 and a planning unit 212 for implementing the various inventive principles of the present invention as previously explained herein in connection with FIGS. 1-17. In general terms, setup unit 211 performs all tasks necessary to construct an configuration space node structure ("CSDS") appropriate for the particular path planning application within data storage medium 220, and planning unit 212 propagates cost waves as needed to fill the configuration space node structure with costs values as a function of the explicit discrete parameter values and/or the heuristic values in accordance with the present invention as desired for the particular path planning application. The result is an optimal path 240 in a format suitable for the particular path planning application.

While various embodiments of the present invention have been illustrated and described, it will be understood by those skilled in the art that the methods and the system as described herein are illustrative, and various changes and modifications may be made and equivalents may be substituted for elements thereof without departing from the true scope of the present invention. In addition, many modifications may be made to adapt the teachings of the present invention to entity path planning without departing from its central scope. Therefore, it is intended that the present invention not be limited to the particular embodiments disclosed as the best mode contemplated for carrying out the present invention, but that the present invention include all embodiments falling within the scope of the appended claims.

The invention claimed is:

1. A method for planning a path according to a path plan application, the method, comprising:
constructing a configuration space node structure within a data storage medium, the configuration space node structure representing a discretized configuration space including a plurality of nodes characterized by at least one parameter,
wherein the discretized configuration space is one of a two-dimensional discretized configuration space or a three-dimensional discretized configuration space; and
augmenting the configuration space node structure as constructed within the data storage medium with discrete parameter values explicitly quantifying at least one of a location and an orientation of each node of the configuration space node structure.

2. The method of claim 1, wherein the discrete parameter values are derived from a discrete sampling of a neighborhood corresponding to the discretized configuration space.

3. The method of claim 1, further comprising:
propagating cost waves in the configuration space node structure to fill at least a portion of the configuration space node structure with cost values as a function of the discrete parameter values.

4. The method of claim 3, wherein the configuration space node structure is augmented with the discrete parameter values prior to the propagation of the cost waves in the configuration space node structure.

5. The method of claim 3, wherein the configuration space node structure is augmented with the discrete parameter values in response to the propagation of the cost waves in the configuration space node structure.

6. The method of claim 1, further comprising:
propagating cost waves in the configuration space node structure to fill at least a portion of the configuration space node structure with heuristic values representing a search guide through a free space region of the discretized configuration space.

7. The method of claim 6, wherein the heuristic values are derived from a neighborhood configuration connecting each node of the configuration space node structure corresponding to the free space region of the discretized configuration space.

8. A system, comprising:
a data storage medium and a data processing device for planning an optimal path according to a path planning application;
wherein the data processing device is operable to construct a configuration space node structure within the data storage medium, the configuration space node structure representing a discretized configuration space including a plurality of nodes characterized by at least one parameter;
wherein the discretized configuration space is one of a two-dimensional discretized configuration space or a three-dimensional discretized configuration space; and
wherein the data processing device is further operable to augment a construction of the configuration space node structure within the data storage medium with discrete parameter values explicitly quantifying at least one of a location and an orientation of each node of the configuration space node structure.

9. The system of claim 8, wherein the data processing device is further operable to derive the discrete parameter values from a discrete sampling of a neighborhood corresponding to the discretized configuration space.

10. The system of claim 8, wherein the data processing device is further operable to propagate cost waves in the configuration space node structure to fill at least a portion of the configuration space node structure with cost values as a function of the discrete parameter values.

11. The system of claim 10, wherein the configuration space node structure is augmented with the discrete parameter values prior to the propagation of the cost waves in the configuration space node structure.

12. The system of claim 10, wherein the configuration space node structure is augmented with the discrete parameter values in response to the propagation of the cost waves in the configuration space node structure.

13. The system of claim 8, wherein the data processing device is further operable propagate cost waves in the configuration space node structure to fill at least a portion of the configuration space node structure with heuristic values representing a search guide through a free space region of the discretized configuration space.

14. The system of claim 13, wherein the heuristic values are derived from a neighborhood configuration connecting each node of the configuration space node structure corresponding to the free space region of the discretized configuration space.

15. A data processing device, comprising:
a setup unit and a path planning unit for planning an optimal path according to a path planning application;
wherein the setup unit is operable to construct a configuration space node structure within a data storage medium, the configuration space node structure representing a discretized configuration space including a plurality of nodes characterized by at least one parameter;
wherein the discretized configuration space is one of a two-dimensional discretized configuration space or a three-dimensional discretized configuration space; and
wherein at least one of the setup unit and the path planning unit is operable to augment construction of the configuration space node structure within the data storage medium with discrete parameter values explicitly quantifying at least one of a location and an orientation of each node of the configuration space node structure.

* * * * *